Figure 1:
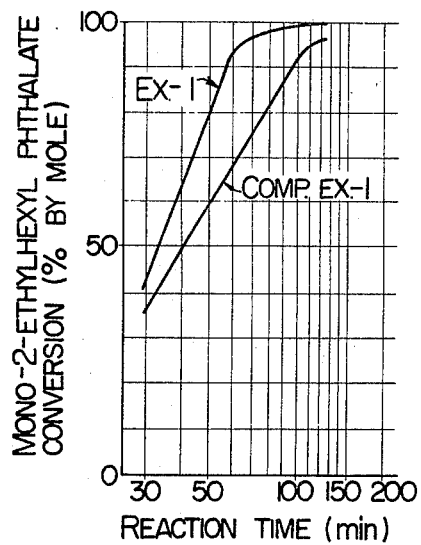

United States Patent [19]

Abe et al.

[11] 4,334,080

[45] Jun. 8, 1982

[54] PROCESS FOR PRODUCING BENZENE CARBOXYLIC ACID ESTER

[75] Inventors: Koichi Abe; Masami Ishihara; Thuyoshi Watanabe, all of Kurashiki, Japan

[73] Assignee: Mitsubishi Gas Chemical Co., Ltd., Tokyo, Japan

[21] Appl. No.: 210,058

[22] Filed: Nov. 24, 1980

[30] Foreign Application Priority Data

Nov. 26, 1979 [JP] Japan .................................. 54/152650

[51] Int. Cl.³ ............................................. C07C 67/08
[52] U.S. Cl. ...................................... 560/99; 560/103
[58] Field of Search ................................. 560/99, 103

[56] References Cited

FOREIGN PATENT DOCUMENTS 48-49783  7/1973  Japan .

OTHER PUBLICATIONS

Advances in Chemistry, Series 48, pp. 76–86, (1965).

Primary Examiner—Natalie Trousof
Assistant Examiner—Vera C. Clarke
Attorney, Agent, or Firm—Armstrong, Nikaido, Marmelstein & Kubovcik

[57] ABSTRACT

Benzenecarboxylic acid ester is produced at a higher reaction rate in a better yield in a shorter time by reacting benzenecarboxylic acid having 8 to 10 carbon atoms or its anhydride with aliphatic alcohol having 7 to 11 carbon atoms in the presence of amorphous aluminum compound as a catalyst and an alkali metal compound as a promoter.

5 Claims, 3 Drawing Figures

PROCESS FOR PRODUCING BENZENE CARBOXYLIC ACID ESTER

This invention relates to a process for producing benzenecarboxylic acid ester at a higher reaction rate than that with the conventional process using a catalyst of crystalline aluminum compound-alkali metal compound system.

Acid catalysts such as sulfuric acid and paratoluenesulfonic acid are known as catalyst for commercially producing benzenecarboxylic acid esters, but have such disadvantages as occurrence of side reaction, for example, dehydration of raw material alcohol, byproduction of colored impurities, etc. Thus, various selective catalysts of organometal compounds, metal oxides, etc. free from the disadvantages of the acid catalysts have been so far proposed.

The present inventors have studied, among others, alumina catalysts. The alumina catalyst is used as an aluminum compound represented by $Al_2O_3 \cdot nH_2O$ or $Al(OH)_3$ together with an alkali metal compound such as caustic soda, etc., and has a good selectivity but has such a disadvantage as a low esterification reaction rate. Thus the alumina catalyst is less advantageous for the commercial application (Plasticization and Plasticizer Processes, Advances in Chemistry Series 48, pages 76–87, published by American Chemical Society, 1965).

To overcome the disadvantage, it is proposed to add a lithium compound as third component to the alumina catalyst (Japanese Laid-open Patent Application Specification No. 49738/73), where 0.02–0.15 g of a lithium compound is added to one mole of carboxyl group of the raw material. The lithium compound is expensive.

The present inventors have investigated not the third component, but a suitable type of aluminum compound, and as a result the present inventors have found that the desired ester can be obtained at a higher reaction rate in a better yield in a shorter time when an amorphous aluminum compound represented by the general formula, $Al_x(CO_3)_y(OH)_z \cdot nH_2O$ (where $x:y = 8-6:1$; $x:z = 11-8:4-3$) is used in place of $Al_2O_3 \cdot nH_2O$ or $Al(OH)_3$.

The present invention provides a process for producing benzenecarboxylic acid ester which comprises reacting benzenecarboxylic acid having 8–10 carbon atoms or the carboxylic acid anhydride with aliphatic alcohol having 7–11 carbon atoms in the presence of amorphous aluminum compound as a catalyst and an alkali metal compound as a promoter, thereby producing the corresponding ester.

Quite different from crystalline aluminum compound obtained according to any of ordinary acid and alkali processes, whose crystallinity can be confirmed by X ray diffraction, the aluminum compound used as a catalyst in the present invention is a compound represented by the following general formula:

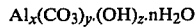

$$Al_x(CO_3)_y(OH)_z \cdot nH_2O$$

where $x:y = 8-6:1$; $x:z = 11-8:4-3$), which will be hereinafter referred to as "the aluminum compound of the present invention".

In the present invention, an alkali metal compound is used as a promoter. The promoter includes caustic soda, sodium carbonate, sodium hydrogen carbonate, caustic potash, potassium carbonate, and potassium hydrogen carbonate.

The benzenecarboxylic acid having 8–10 carbon atoms or the carboxylic acid anhydride used in the present invention includes benzene-1,2-dicarboxylic acid, benzene-1,2,4-tricarboxylic acid, benzene-1,2,4,5-tetracarboxylic acid, benzene-1,2,3,5-tetracarboxylic acid and their anhydrides.

The aliphatic alcohol having 7–11 carbon atoms used in the present invention includes 2-ethylhexanol, n-octanol, a mixture of straight chain aliphatic alcohols having 7–9 carbon atoms, a mixture of straight chain aliphatic alcohols having 9–10 carbon atoms, and a mixture of straight chain aliphatic alcohols having 9–11 carbon atoms.

According to the present invention, esterification reaction is carried out under the following conditions:

(1) 1.1–1.8 moles of the raw material alcohol to 1 mole of the carboxyl group of the raw material benzenecarboxylic acid, (2) 0.01–0.3 grams, preferably 0.02–0.2 grams, of the amorphous aluminum compound as aluminum to one mole of the carboxyl group of the raw material benzenecarboxylic acid, (3) 0.01–0.90 grams, preferably 0.02–0.5 grams, of the alkali metal compound as alkali metal to one mole of the carboxyl group of the raw material benzenecarboxylic acid, (4) Temperature of 180°–250° C. under the normal pressure or subatmospheric pressure, while removing the formed water to the outside of reaction system through azeotropic boiling of raw material alcohol.

In the present invention, a reaction rate is higher than that in the conventional process using an alumina-alkali catalyst, and thus commercial application can be more readily carried out. Furthermore, the present catalyst is excellent in selectivity, and side reactions such as byproduction of colored impurities or dehydration of the raw material alcohol at the esterification reaction hardly occur. As a result, the recovered alcohol can be reused as such as the raw material, and purification operation such as distillation or decolorization can be omitted. That is, product esters with a good color tone can be obtained. Furthermore, the present catalyst is deposited mostly in the reaction solution after the esterification reaction, and thus can be separated by mechanical operation such as filtration, etc., and the resulting cake can be reused as such as the esterification reaction catalyst.

The esters formed according to the esterification reaction include diheptyl phthalate, dioctyl phthalate (di-2-ethylhexyl phthalate), phthalates of straight chain, mixed dialkyls having each 7–9 carbon atoms, phthalates of straight chain mixed dialkyls having each 9–11 carbon atoms, trioctyl trimellitate and tetraoctyl pyromellitate.

The present invention will be described in detail below, referring to Examples, Comparative Examples and Drawings.

Figure 2:
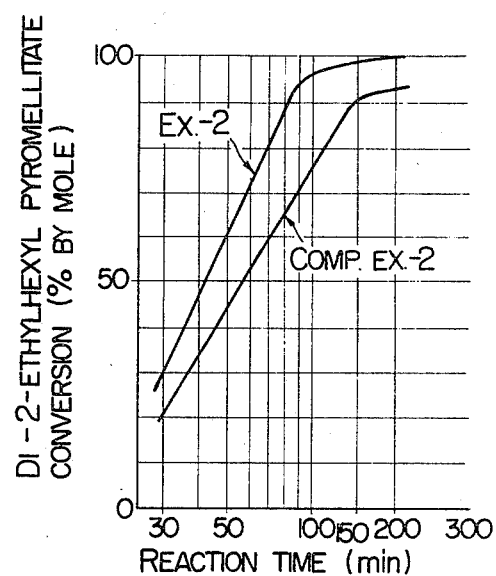
Figure 3:
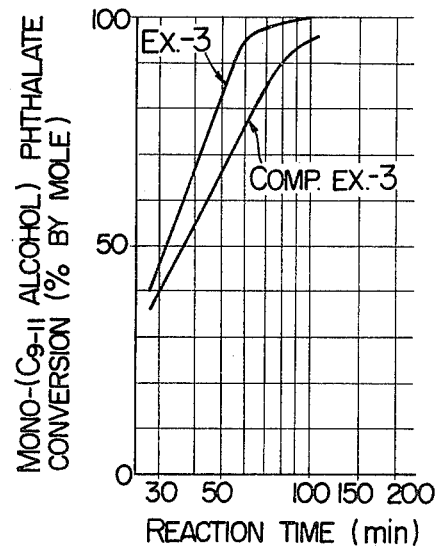

FIGS. 1–3 show relationships between conversions and reaction time of Examples 1–3 and Comparative Examples 1–3.

EXAMPLE 1

325 Parts by weight of 2-ethylhexanol and 148 parts by weight of phthalic anhydride were added to a glass flask with a reflux condenser, a water separator, a stirrer and a thermometer, and dissolved under heating to a temperature of 120° C. and stirring to produce mono-2-ethylhexyl phthalate. Then, 0.17 parts by weight of the aluminum compound of the present invention as aluminum, and 0.35 part by weight of caustic soda as sodium were added, and diesterification was carried out at an increasing temperature from 180° to 250° C. under the atmospheric pressure to produce di-2-ethylhexyl phthalate.

Change in mono-2-ethylhexyl phthalate conversion with time was measured. Results are shown in FIG. 1. The conversion can be regarded as substantially equal to product yield in the esterification reaction. That is, unconversion means that there are still unreacted substances.

EXAMPLE 2

325 Parts by weight of 2-ethylhexanol and 109 parts by weight of pyromellitic anhydride were added to the same glass flask as used in Example 1, and dissolved under heating to a temperature of 150° C. and stirring to produce di-2-ethylhexyl pyromellitate. Then, 0.17 parts by weight of the aluminum compound of the present invention as aluminum and 0.35 parts by weight of caustic soda as sodium were added thereto, and esterification was carried out at an increasing temperature from 180° to 235° C. under the atmospheric pressure to produce di-2-ethylhexyl phthalate.

Change in mono-2-ethylhexyl pyromellitate with time was measured. Results are shown in FIG. 2.

COMPARATIVE EXAMPLE 1

Mono-2-ethylhexyl phthalate was prepared in the same manner as in Example 1, and 0.21 parts by weight of aluminum hydroxide as aluminum and 0.42 parts by weight of caustic soda as sodium were added thereto. Diesterification was carried out in the same manner as in Example 1 to produce di-2-ethylhexyl phthalate.

Change in mono-2-ethylhexyl phthalate with time was measured. Results are shown in FIG. 1.

COMPARATIVE EXAMPLE 2

Di-2-ethylhexyl pyromellitate was prepared in the same manner as in Example 2, and 0.21 parts by weight of aluminum oxide ($Al_2O_3$ made by Wako Chemicals K.K., Japan) as aluminum and 0.42 parts by weight of caustic soda as sodium were added thereto, and esterification was carried out in the same manner as in Example 2 to produce tetra-2-ethylhexyl pyromellitate.

Change in di-2-ethylhexyl pyromellitate with time was measured. Results are shown in FIG. 2.

EXAMPLE 3

400 Parts by weight of mixed straight chain alcohols having 9-11 carbon atoms (average molecular weight: 160) and 148 parts by weight of phthalic anhydride were added to the same glass flask as used in Example 1, and dissolved under heating to a temperature of 120° C. and stirring to produce monoester. Then, 0.17 parts by weight of the aluminum compound of the present invention as aluminum and 0.35 parts by weight of caustic soda as sodium were added thereto, and diesterification was carried out at an increasing temperature from 180° to 250° C. under the atmospheric pressure.

Change in monoester conversion with time was measured. Results are shown in FIG. 3.

COMPARATIVE EXAMPLE 3

Monoester phthalates of mixed straight chain alcohols having 9-11 carbon atoms were prepared in the same manner as in Example 3, and then 0.21 parts by weight of aluminum hydroxide as aluminum and 0.42 parts by weight of caustic soda as sodium were added thereto. Diesterification was carried out in the same manner as in Example 3.

Change in monoester conversion with time was measured. Results are shown in FIG. 3.

As is evident from comparison of Examples 1-3 with Comparative Examples 1-3, as illustrated in FIGS. 1-3, the present process is distinguished in reaction rate and yield.

What is claimed is:

1. A process for producing benzenecarboxylic acid ester which comprises reacting benzenecarboxylic acid having 8 to 10 carbon atoms or its anhydride with aliphatic alcohol having 7 to 11 carbon atoms in the presence of an amorphous aluminum compound represented by the formula $Al_x(CO_3)_y(OH)_z \cdot nH_2O$, wherein $x:y = 8-6:1$ and $x:z = 11-8:4-3$, as a catalyst and an alkali metal compound as a promoter.

2. A process according to claim 1, wherein the alkali metal compound is caustic soda, sodium carbonate, sodium hydrogen carbonate, caustic potash, potassium carbonate or potassium hydrogen carbonate.

3. A process according to claim 1, wherein the benzenecarboxylic acid having 8 to 10 carbon atoms is benzene-1,2-dicarboxylic acid, benzene-1,2,4-tricarboxylic acid, benzene-1,2,4,5-tetracarboxylic acid, benzene-1,2,3,5-tetracarboxylic acid or their anhydride.

4. A process according to claim 1, wherein the aliphatic alcohol having 7 to 11 carbon atoms is 2-ethylhexanol, n-octanol, a mixture of straight chain aliphatic alcohols having 7 to 9 carbon atoms, a mixture of straight chain aliphatic alcohols having 9 to 10 carbon atoms, or a mixture of straight chain aliphatic alcohols having 9 to 11 carbon atoms.

5. A process according to claim 1, wherein the reaction is carried out in a ratio of 1.1 to 1.8 moles of the aliphatic alcohol to one mole of carboxyl group of the benzenecarboxylic acid, a ratio of 0.01 to 0.3 grams of the amorphous aluminum compound as aluminum to one mole of carboxyl group of the benzenecarboxylic acid, a ratio of 0.01 to 0.90 grams of the alkali metal compound as alkali metal to one mole of carboxyl group of the benzene carboxylic acid at a temperature of 180° to 250° C. under the normal pressure or a subatmospheric pressure, while removing formed water to the outside of reaction system by azeotropic boiling with the aliphatic alcohol.

* * * * *